United States Patent [19]

Buret et al.

[11] Patent Number: 5,634,365

[45] Date of Patent: Jun. 3, 1997

[54] PROCESS ALLOWING BACKGROUND NOISE TO BE REDUCED DURING EDDY-CURRENT TESTING OF METAL TUBES, AND TUBES PRODUCED USING THIS PROCESS

[75] Inventors: Jean-Louis Buret; Denis Vuillaume, both of Montbard, France

[73] Assignee: Valinox Nucleaire, Paris, France

[21] Appl. No.: 279,889

[22] Filed: Jul. 26, 1994

[30] Foreign Application Priority Data

Aug. 2, 1993 [FR] France .................................. 93 09694

[51] Int. Cl.$^6$ ............................................. B21D 7/02
[52] U.S. Cl. .............................. 72/214; 72/227; 72/16.8; 72/31.06; 138/39; 324/225; 324/238; 324/207.23
[58] Field of Search ................. 324/207.18, 207.23, 324/225, 238, 237, 240; 318/37, 39, 177; 72/9, 31, 33, 41, 214, 227, 283, 413

[56] References Cited

U.S. PATENT DOCUMENTS 4,030,333   6/1977   Bellmann et al. .
5,101,366   3/1992   Cueman et al. ............................ 72/33

FOREIGN PATENT DOCUMENTS 0 390 482   10/1990   European Pat. Off. .
0 445 983    9/1991   European Pat. Off. .
2 585 593    2/1987   France .
86/01896     3/1986   WIPO .

*Primary Examiner*—W. Donald Bray
*Attorney, Agent, or Firm*—Oblon, Spivak, McClelland, Maier & Neustadt, P.C.

[57] ABSTRACT

The process relates to the aptitude for detectability of defects using eddy-currents on metal tubes cold laminated using a pilger mill and relates more particularly to the possibility of reducing the background noise and increasing the ratio between a standard signal and this background noise.

The process consists of carrying out, after reduction in section by at least 30% in a cold pilger mill, a hollow drawing pass with a reduction in the external diameter of approximately 0.1% to 5%. The signal/background noise ratio can in this way be multiplied by a factor of between 2 and 3.7, in the case of a series of tubes made of INCO 690 alloy, as shown in the single figure.

The invention also relates to tubes produced using this process.

Application in production of steam generating tubes for nuclear power stations.

15 Claims, 1 Drawing Sheet

PROCESS ALLOWING BACKGROUND NOISE TO BE REDUCED DURING EDDY-CURRENT TESTING OF METAL TUBES, AND TUBES PRODUCED USING THIS PROCESS

BACKGROUND OF THE INVENTION

1. Field of the Invention

The process which is the subject-matter of the invention relates to the detection of defects using eddy-currents in metallic tubes cold-rolled using a pilger mill.

2. Discussion of the Background

A process is known for detection using eddy-currents which is applicable in particular to the testing of small diameter tubes. Such tubes are used more especially in heat exchangers for the production of steam using pressurised water passing through these tubes in a closed circuit from a nuclear reactor. These tubes are most often made with certain stainless steels such as a type 316 steel (ASTM A312 standard) or INCO 600 and 690 or otherwise other alloys with a high Ni content, such as INCOLOY 800 and INCOLOY 825 (ASTM B163 standard), INCO and INCOLOY being trademarks of HUNTINGTON ALLOYS.

The process for detection of defects using eddy-currents is used in a systematic manner for 100% testing for the defects which these tubes may present either at the time when they are supplied or subsequently in tests carried out directly on the tubes assembled on the exchangers when there are stoppages, usually programmed, for checking operating performance.

The conditions for carrying out such eddy-current tests are the subject of regulations proposed, for example, by ASME and applied most often by agreement between the producers and users, in order to ensure the most efficient detection possible of the defects presented by the tubes. These tests can be carried out either with external sensors or with internal sensors. Standard defects are used, in general composed of small diameter holes radially piercing the wall of these tubes through the whole thickness or a fraction thereof, for comparing eddy-current responses thereto with responses received in examining a tube with unknown defects.

For eddy-current testing of the in-service inspection type, the tubes being assembled in the exchangers, detection is carried out from the interior of the tube by means of an internal sensor with a diameter slightly less than the diameter of said tube, which is displaced at a relative speed of, for example, 0.30 m/s.

The sensor is generally composed of 2 coils mounted in a Wheatstone bridge and used in differential mode. The sensor is supplied with high frequency current in a typical range of 1 00 to 700 KHz.

By way of example, the exchanger tubes used for the production of steam from pressurised water most often have an external diameter of approximately 0.75 to 1.00 inch (19.05 to 25.4 ram) and a wall thickness of approximately 0.026 to 0.043 inches, that is to say approximately 0.66 to 1.1 mm.

It has been noted that the significant reduction in section, generally greater than 50% and which can exceed 70%, carried out cold in one pass using a pilger mill leads to a very significant work-hardening which gives the advantage of avoiding an excessive coarsening of the grain of the alloy, during solid solution annealing which is most often carried out to limit the risks of stress corrosion.

It has also been noted that cold-rolling carried out in this manner is the cause of a relatively large background noise which appears at the terminals of the eddy-current sensor receiving means. The background noise reduces the signal/background noise ratio and thus tends to mask low amplitude defects.

It is possible to lower the background noise by modifying the rolling conditions but it is most often necessary to reduce the rolling speed, and therefore productivity; despite this, the reduction in the background noise is often insufficient to achieve the signal/background noise ratio required for a standard defect of set dimensions.

The possibility has been looked into of reducing, in a significant manner, the background noise observed during eddy-current testing in an internal or external sensor of tubes cold-worked using a pilger mill. It has also been sought not to have to reduce the rolling speed, and also not to have to lessen the amount of reduction and thus of the work-hardening before the final heat solution treatment.

Finally, the possibility has been looked into of perfecting a process for section reduction before final annealing, generally applicable to the production of all types of small diameter, long length metallic tubes allowing eddy-current testing for defects by external or internal sensor with a high signal/background noise ratio.

SUMMARY OF THE INVENTION

The process which is the subject-matter of the invention allows all of the desired results to be achieved.

The process allows all the advantages of cold rolling with a pilger mill to be retained, while allowing the background noise to be considerably reduced and the signal/background noise ratio to be increased in a very significant manner.

According to the process, before the final heat treatment comprising annealing of the metallic tube proposed to be tested for defects using eddy-currents, a final cold rolling in the pilger mill is usually carried out with an amount reduction in section equal to at least 30%.

A hollow drawing pass, also cold, is then carried out on the tube thus work-hardened, allowing the final external diameter aimed for to be obtained.

This reduction of the external diameter is at least of 0.1% and not greater than 5% and advantageously between 0.2% and 3% and more specifically between 0.2% and 0.5%.

It has been noted that this reduction in the external diameter is not accompanied by a very appreciable variation in the thickness.

The reduction in diameter is accompanied by an elongation proportional to the reduction of the section of the tube. Given that the tube has been very highly work-hardened by milling, the reduction in the diameter of the tube is preferably limited to approximately 0.2 to 0.5%.

In order to obtain the diameter aimed for, it is necessary to select a die with an appreciably smaller diameter due to the high elastic limit of highly work-hardened metal.

In carrying out systematic eddy-current testing of the tube manufactured in this manner, on the one hand in the state where it is work-hardened by passing through the pilger mill before hollow drawing and on the other hand after hollow drawing and before heat treatment, it has been noted, quite unexpectedly, that there is a considerable reduction in background noise following the light hollow drawing pass, particularly during use of an internal sensor.

The higher the background noise, the greater this reduction.

As a result, even in the case where the tube which has just undergone a reduction in section of at least 50% and preferably of at least 70% in the pilger mill presents a relatively high background noise, it is generally possible to sufficiently reduce the background noise, by virtue of the light hollow drawing pass, and to obtain a ratio between the selected standard signal and the background noise greater than the limit considered acceptable for this ratio.

The hollow drawing pass allows not only the average background noise level of the tube to be reduced, but also reduction in the variation of this background noise.

In practice, the eddy-current sensor is standardised in such a manner as to provide a signal of a determined strength for a standard defect which is, for example, a radial hole with a defined diameter, piercing right through the wall of the tube.

From this standard signal the background noise, and the signal to background noise ratio are measured. The signal/background noise ratio does not have an absolute value as it depends upon the section of the tube, the nature of the alloy and the dimensional characteristics of the standard defect. It is not possible therefore to specify in a general manner the factor of the increase of this ratio following the hollow drawing pass. Nevertheless, a progressive rise in this factor of increase as a function of the initial background noise is observed.

The process according to the invention is thus a genuine means for reducing the background noise and thus of increasing the signal background noise ratio, which is all the more efficient the greater the initial background noise.

Tubes produced using the process according to the invention can thus be considered as safety tubes because of their particular aptitude for the detection of small defects using eddy-currents.

The invention also relates to safety tubes with eddy-current tested characteristics for particular applications, made from austenitic stainless steel or from metals or alloys, with a relatively small diameter, the final reduction in section before final heat treatment of which comprises a reduction of at least 30% in a pilger mill, cold, followed by a hollow drawing pass with a reduction in diameter of 0.1% to 5%.

Advantageously this reduction in diameter is between 0.2% and 3% and more specifically between 0.2% and 0.5%.

The tubes are, by way of example, made of a stainless steel or of an alloy containing at least 40% by mass of the total of at least one element from the group comprising Ni, Mo and Cr.

It is possible to carry out the hollow drawing pass replacing the classic drawing die with at least one die with rollers. Several of these dies can be arranged in series, one behind the other, with different angular inclination around the axis of drawing in order to give the tube a perfect surface of revolution. The amount of reduction of the diameter is of the same order of size as in the case of a classic die.

Other ways of carrying out the process according to the invention and of manufacture of the product according to the invention can be carried out without departing from the scope of the invention.

BRIEF DESCRIPTION OF THE DRAWING

The example and the single figure hereafter describe in a non-limiting manner a particular means of carrying out the process according to the invention and of manufacture of the product according to the invention.

Single figure: The single figure is a diagram which shows a line of correlation between the maximum background noise measured by eddy-currents with an internal sensor in tubes leaving a pilger mill and that of these same tubes after a hollow drawing pass.

DESCRIPTION OF THE PREFERRED EMBODIMENTS

Figure 1:
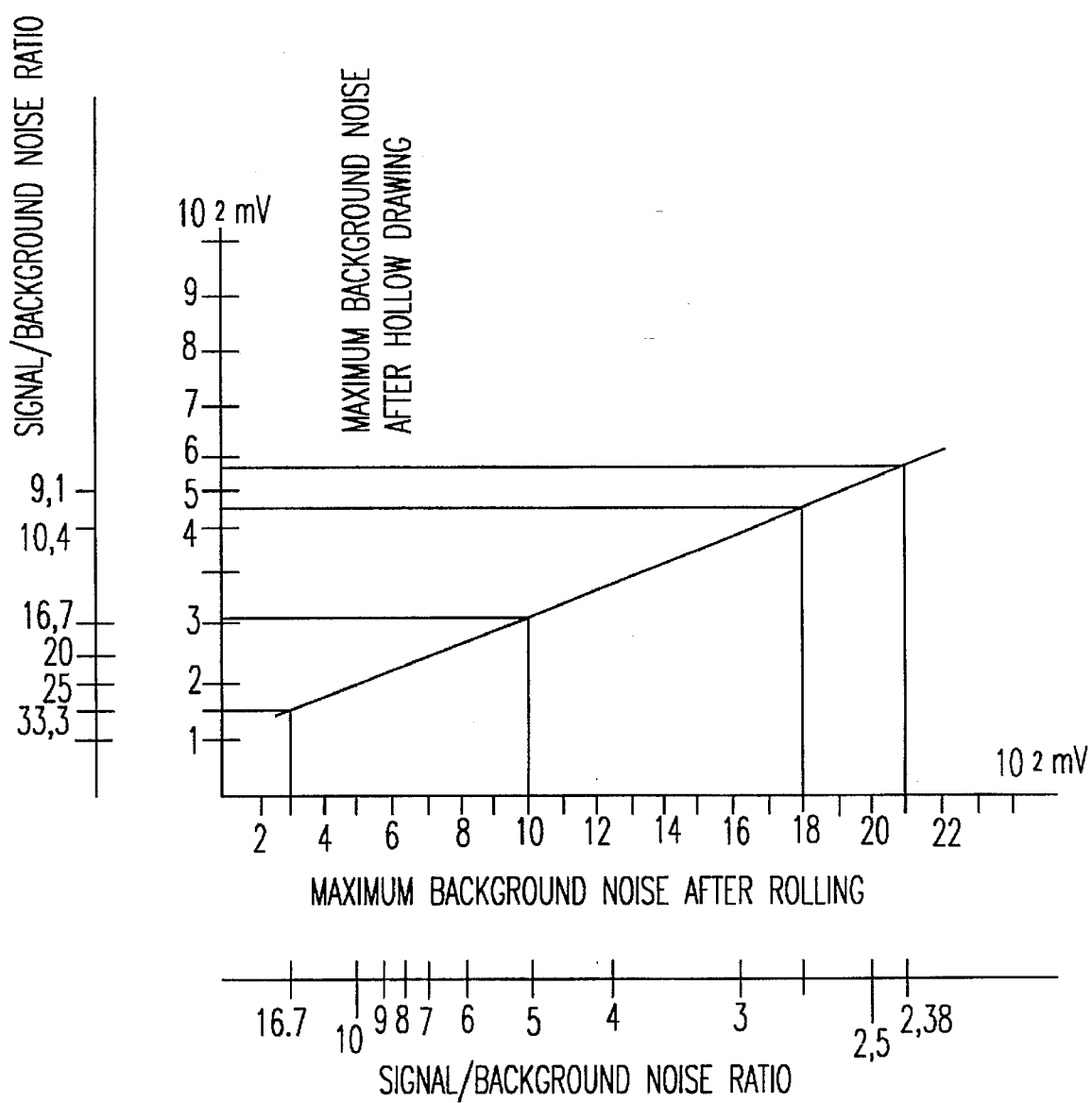

The maximum background noise of a tube is defined by its average background noise over a length of approximately 500 mm in the area of the tube presenting the highest background noise.

Example: A batch of hollow blanks is produced in a known manner by hot extrusion, made of an INCO 690 alloy containing a percentage by mass of Ni$\geq$58.0; Fe 7.0 to 11.0; Cr 27.0 to 31.0.

These blanks are subsequently reduced cold in the pilger mill to an external diameter of 37.5 mm and a thickness of 2.5 min.

After annealing, these intermediate blanks are rolled in a cold pilger mill with an amount of reduction in section of 77.3%, to an external diameter of 19.14 mm and a thickness of 1.10 min.

Using an internal eddy-current sensor, the maximum background noise and the ratio between the amplitude of the signal corresponding to a standard defect and this maximum background noise is measured for each tube manufactured in this manner. A single radial hole which is 1.32 mm in diameter, passing through the wall of a tube section is used as a standard defect. The exciting current of the sensor has a frequency of 550 KHz and the excitation voltage is adjusted to produce a pick-up voltage of 5 V when the sensor passes by the level of the defect. It has been noted that the maximum background noise in the batch of tubes reduced in this manner in a pilger mill is on average 920 mV, that is an average signal/background noise ratio for the whole batch of 5.4.

Subsequently according to the invention cold reduction of the external diameter by hollow drawing out of these same tubes across a die of a suitable diameter is carried out in a single pass, which allows a final diameter of 19.07 mm to be obtained. It has been noted that the reduction in diameter by 0.07 mm, that is to say 0.39% of the initial diameter, is not accompanied by a noticeable variation in thickness and thus only by a corresponding lengthening. The total reduction of the section starting at the initial diameter of 37.5 mm is thus 77.7%. Once again, the maximum background noise and the signal/maximum background noise ratio is measured under the same conditions using an eddy-current sensor. It has been noted that the maximum background noise is lowered on average to approximately 290 mV, the signal/background noise ratio being raised to approximately 17.2.

It can thus be seen that on average the signal/maximum background noise ratio is multiplied by more than 3 by virtue of the process according to the invention.

The single figure shows the correlation which exists between the average values of the maximum background noise arid the signal/maximum background noise ratio measured for each of the tubes in the batch studied. The values given on the x-axis relate to the tubes when cold rolled in the pilger mill and the values given on the y-axis relate to the same tubes after having been subjected to a hollow drawing pass, also cold, to the final diameter of 19.07 min.

It can be seen that in general the hollow drawing pass not only reduces the maximum background noise and raises the signal/maximum background noise ratio, but also reduces the variation in the results.

Thus a maximum background noise level of 300 mV is reduced to 150 mV, that is to say divided by 2, while at the other end of the scale a maximum background noise level of approximately 1,800 mV is reduced to approximately 480 mV, that is to say divided by 3.75.

In comparing the signal/maximum background noise ratios, it can be seen than an initial ratio of 16.7 for a maximum background noise of 300 mV is multiplied by 2 and thus reaches 33.3, whereas a ratio of 2.8 corresponding to a maximum background noise of 1,800 mV is brought to 10.4, that is to say multiplied by 3.7.

As a result the light hollow drawing pass allows, in the majority of cases, the tubes obtained using a pilger mill to be given the desired characteristics of aptitude for eddy-current testing.

While the tests described in this example were carried out on a nickel-based alloy, the process is also applicable to stainless steels or to materials cited in the present description.

It should be noted that the hollow drawing pass required by the process according to the invention, taking into account (the small amount of deformation necessary in order to carry out the process, particularly in the deformation range of 0.2% to 0.5%, has the advantage of retaining the favourable properties obtained by the range of cold pilger milling in the tubes, while considerably improving the conditions for eddy-current testing, particularly with an internal sensor.

More generally, the hollow drawing pass according to the invention has, because on one side it is a hollow pass and on the other side because of the specific characteristics of said pass, a certain number of supplementary advantages and in particular:

it modifies as less as possible the former manufacturing route of the tube, the carrying out of a hollow drawing pass avoids using a lubricant which enters and disturbs the tube inside surface and the elimination of which is essential and difficult for all processes in which an inside mandrel, either short or long or a plug is used for the drawing operation.

the absence of inside mandrel or plug also totally avoids the chatter or jamming of the drawn tube, which chatter or jamming is especially difficult to control for tubes of long length and small diameter drawn on short inside mandrel or on plug, said chatter or jamming causing local dimension variations which constitute sources of background noise.

All these advantages make the claimed process a particularly efficient one, in particular as regards the economic point of view, to solve the problems which the invention has as background.

What is claimed as new and desired to be secured by Letters Patent of the United States is:

1. A process for increasing the signal/background noise ratio measured by an eddy-current sensor compared to the signal/background noise ratio attained when the eddy-current sensor is used for testing a metallic tube with a small diameter which has been formed to size by being subjected to a cold reduction of at least 30% using a cold pilger mill, said process comprising subjecting the metallic tube to at least one hollow drawing pass carried out, cold, thereon to further reduce the external diameter of the metallic tube by at least 0.1% and at most by 5% to thereby attain said increased signal/background noise ratio upon inspection by an eddy-current sensor.

2. A process according to claim 1, characterized in that the sensor used is an internal sensor.

3. A process according to claim 1, characterized in that the sensor used is an external sensor.

4. A process according to claim 1, characterized in that the reduction in external diameter of the metallic tube is between 0.2% and 3%.

5. A process according to claim 1, characterized in that the reduction in external diameter of the metallic tube is between 0.2% and 0.5%.

6. A process according to claim 1, characterized in that the amount of reduction using a pilger mill is at least 50%.

7. A process according to claim 1, characterized in that the metallic tube is made of an austenitic stainless steel.

8. A process according to claim 1, characterized in that the metallic tube is made of an alloy containing at least 40% by mass, in total, of at least one element from the group comprising Ni, Cr, Mo.

9. A process according to claim 1, characterized in that the metallic tube is made of an alloy containing a mass percentage of Ni$\geq$58.0; Fe 7.0 to 11.0; Cr 27.0 to 31.0.

10. A metallic safety tube in metal or alloys with a relatively small diameter, being formed to size by a reduction in section of at least 30% using a cold pilger mill followed by a hollow drawing pass in a manner such as to reduce its diameter by at least 0.1% and at most 5%.

11. A metallic safety tube according to claim 10, characterized in that the reduction in the external diameter of the tube is between 0.2% and 3% and advantageously between 0.2% an 0.5%.

12. A metallic safety tube according to claim 10 characterized in that it is subjected to a final heat treatment.

13. A metallic safety tube according to claim 11 characterized in that it is subjected to a final heat treatment.

14. A heat exchanger comprising a metallic safety tube according to any one of claims 10, 11, 12 or 13.

15. A heat exchanger according to claim 14 characterized in that the heat exchanger is heated by a circuit of water originating from a nuclear reactor and allows the production of steam.

* * * * *

UNITED STATES PATENT AND TRADEMARK OFFICE
CERTIFICATE OF CORRECTION

PATENT NO. : 5,634,365
DATED : June 03, 1997
INVENTOR(S) : Jean-Louis BURET, ET AL.

It is certified that error appears in the above-indentified patent and that said Letters Patent is hereby corrected as shown below:

In column 1, line 58, change "ram" to --mm--.

In column 4, line 18, change "min" to --mm--.

In column 4, line 23, change "min" to --mm--.

In column 4, line 63, change "min" to --mm--.

In column 5, line 7, change "than" to --that--.

Signed and Sealed this

Thirteenth Day of January, 1998

BRUCE LEHMAN

Attest:

Attesting Officer

Commissioner of Patents and Trademarks